(12) United States Patent
Alimardanov et al.

(10) Patent No.: US 7,476,762 B2
(45) Date of Patent: Jan. 13, 2009

(54) METHODS FOR PREPARING SULFONAMIDE COMPOUNDS

(75) Inventors: Asaf Ragim Alimardanov, Nanuet, NY (US); Jean Schmid, Chester, NY (US); Jay Thomas Afragola, Spring Valley, NY (US); Gulnaz Khafizova, West Nyack, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/788,352

(22) Filed: Apr. 19, 2007

(65) Prior Publication Data
US 2007/0249723 A1 Oct. 25, 2007

Related U.S. Application Data

(60) Provisional application No. 60/793,874, filed on Apr. 21, 2006.

(51) Int. Cl.
C07C 303/00 (2006.01)
C07C 229/00 (2006.01)
C07C 241/00 (2006.01)

(52) U.S. Cl. .............................. 564/86; 560/34; 562/439
(58) Field of Classification Search .................. 560/34; 562/439
See application file for complete search history.

(56) References Cited

U.S. PATENT DOCUMENTS

| | | | |
|---|---|---|---|
| 6,610,734 B2 | 8/2003 | Kreft et al. | |
| 6,657,070 B2 | 12/2003 | Resnick | |
| 6,878,742 B2 | 4/2005 | Kreft et al. | |
| 7,166,622 B2 | 1/2007 | Kreft et al. | |
| 2004/0198778 A1 | 10/2004 | Kreft et al. | |
| 2005/0171180 A1 | 8/2005 | Resnick et al. | |
| 2005/0196813 A1 | 9/2005 | Kreft et al. | |
| 2007/0197800 A1* | 8/2007 | Chan et al. | 549/62 |
| 2007/0197830 A1* | 8/2007 | Chan et al. | 564/393 |
| 2007/0249722 A1* | 10/2007 | Porte et al. | 514/602 |
| 2007/0249869 A1* | 10/2007 | Sellstedt et al. | 564/469 |

FOREIGN PATENT DOCUMENTS

| WO | WO-03/103660 | 12/2003 |
|---|---|---|
| WO | WO-2004/092155 | 10/2004 |

OTHER PUBLICATIONS

Davis et al., "Asymmetric Strecker Synthesis Using Enantiopure Sulfinimines and Diethylaluminum Cyanide: The Alcohol Effect", J. Org. Chem., 61(2):440-441, Jan. 26, 1996.
Enders et al., "Enantioselective Synthesis of 3-Substituted 2-Ketoesters", Angew. Chem. Int. Ed. Engl., 31(5):618-620, 1992.
Enders et al., "Enantioselective Synthesis of Protected Isotetronic Acids", Chem. Eur. J., 4(2):311-320, 1998.
Han et al., "Total Asymmetric Synthesis of Highly Constrained Amino Acids β-Isoproyl-2',6'-Dimethyl-Tyrosines", Tetrahedron Letters, 38(29):5135-5138, 1997.
Speelman et al., "Molecular Structure of a Chiral 3,5-Bridged Pyridine and the Effect of Structure on Circular Dichoric Spectra", J. Org. Chem., 54:1055-1062, 1989.
Umemoto et al., "Synthesis, Properties, and Reactivity of (1H,1H-Perfluoroalkyl) and (1H-Perfluoro-1-alkenyl)aryliodonium Triflates and Their Analogs", Bull. Chem. Soc. Jpn., 60:3307-3313 (Sep. 1987).
Umemoto et al., "1H,1H-Perfluoroalkylation of Enol Silyl Ethers with (1H,1H-Perfluoroalkyl)phenyliodonium Triflates. A New Method for the Preparation of β- and δ-Trifluoromethyl Carbonyl Compounds and Their Higher Perfluoroalkyl Homologues", Bull. Chem. Soc. Jpn., 60:3823-3825 (Oct. 1987).
Evans et al., "Electrophilic Azide Transfer to Chiral Enolates. A General Approach to the Asymmetric Synthesis of α-Amino Acids", J. Am. Chem. Soc., 109:6881-6883 (1987).
Alimardanov, "Practical Asymmetric Synthesis of Trifluoromethyl-Containing Aminoester Using a Modified Davis Protocol", Organic Process Research & Development, 12:424-428 (Epub: May 1, 2008).
Zhang, "Asymmetric Synthesis of Novel α-amino Acids With β-branched Side Chains", Bioorganic & Medicinal Chemistry Letters, 17(9):2401-3 (May 1, 2007 Epub: Feb. 17, 2007).

* cited by examiner

*Primary Examiner*—Daniel M Sullivan
*Assistant Examiner*—Louisa Lao
(74) *Attorney, Agent, or Firm*—Scott K. Larsen; Howson & Howson LLP

(57) ABSTRACT

Methods for preparing substituted phenylsulfonamide compounds of the following structure are provided:

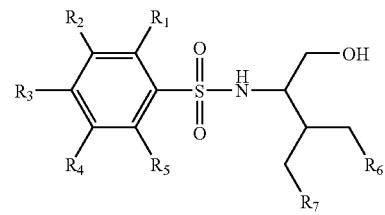

or a pharmaceutically acceptable salt thereof, wherein, $R_1$-$R_7$ are defined herein.

Also provided are methods for preparing compounds of the following structure:

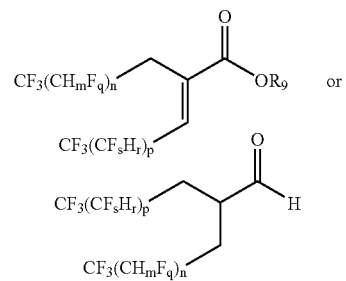

wherein, $R_9$, m, n, p, r, and s are defined herein.

21 Claims, No Drawings

METHODS FOR PREPARING SULFONAMIDE COMPOUNDS

CROSS-REFERENCE TO RELATED APPLICATIONS

This application claims the benefit of the priority of U.S. Provisional Patent Application No. 60/793,874, filed Apr. 21, 2006.

BACKGROUND OF THE INVENTION

Methods for preparing sulfonamide compounds and, specifically, trifluoromethyl-containing sulfonamide compounds are provided herein.

Methods for preparing heterocyclic sulfonamide compounds have been described in U.S. Pat. Nos. 6,878,742 and 6,610,734; and US Patent Publication Nos. US-2004-0198778-A1 and US-2005-0171180-A1. Methods for preparing substituted phenylsulfonamide compounds have also been described in US Patent Application Publication No. US-20040006050-A1.

There continues to be a need for alternate methods for preparing sulfonamide compounds.

SUMMARY OF THE INVENTION

In one aspect, methods for preparing sulfonamide compounds are provided.

In another aspect, methods for preparing substituted phenylsulfonamide compounds and, particularly, trifluoromethyl-containing phenylsulfonamide compounds are provided.

In a further aspect, methods for preparing substituted phenylsulfonamide compounds of the following structure are provided:

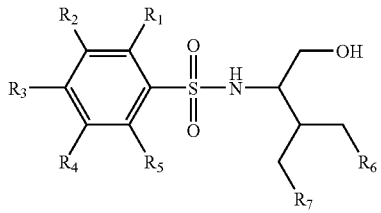

or a pharmaceutically acceptable salt thereof.

In still a further aspect, a method for preparing 4-chloro-N-[(1S)-4,4,4-trifluoro-1-hydroxymethyl-2-(2,2,2-trifluoroethyl)-butyl]benzenesulfonamide, or a pharmaceutically acceptable salt thereof, is provided.

In yet another aspect, methods for preparing compounds of the following structure are provided:

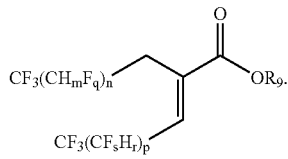

In even a further aspect, methods for preparing compounds of the following structure are provided:

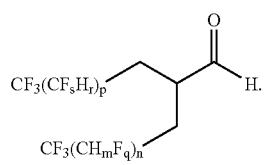

Other aspects and advantages of the invention will be apparent from the following detailed description of the invention.

DETAILED DESCRIPTION OF THE INVENTION

Methods for preparing sulfonamide compounds and particularly substituted phenylsulfonamide compounds are provided. These methods provide higher overall yields of the substituted phenylsulfonamide compounds and are more easily performed on a larger scale. Also provided are methods for preparing the intermediates used therein.

In one embodiment, methods for preparing compounds of the structure are provided:

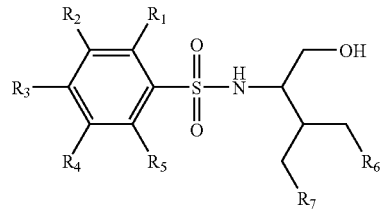

wherein, $R_1$ through $R_5$ are, independently, selected from among hydrogen, halogen, lower alkyl, lower alkoxy, $OCF_3$, $OCF_2H$, $CF_3$, $NO_2$, $CN$, $CH_3CO$, and $SCH_3$; $R_6$ and $R_7$ are, independently, selected from among lower alkyl, $CF_3(CF_sH_r)_p$ and $CF_3(CH_mF_q)_n$; n and p are, independently, 0 to 20; m, q, r, and s are, independently, 0 to 2, provided that m+q=2 and r+s=2. See, Scheme 1.

Scheme 1

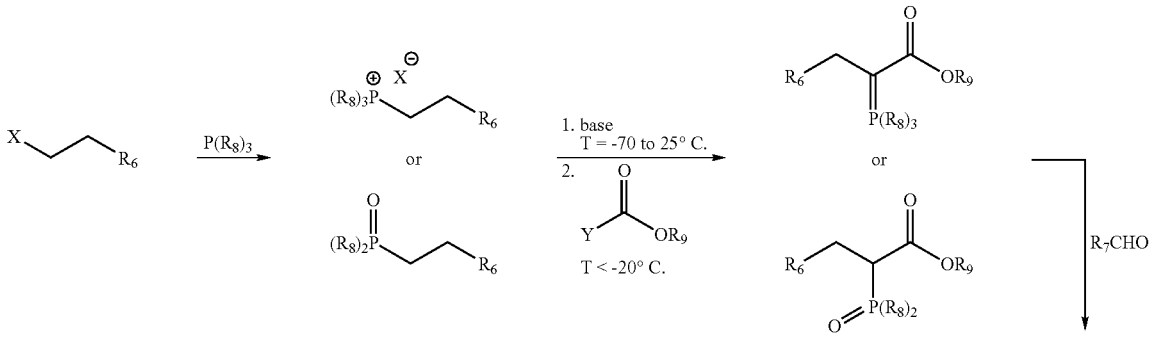

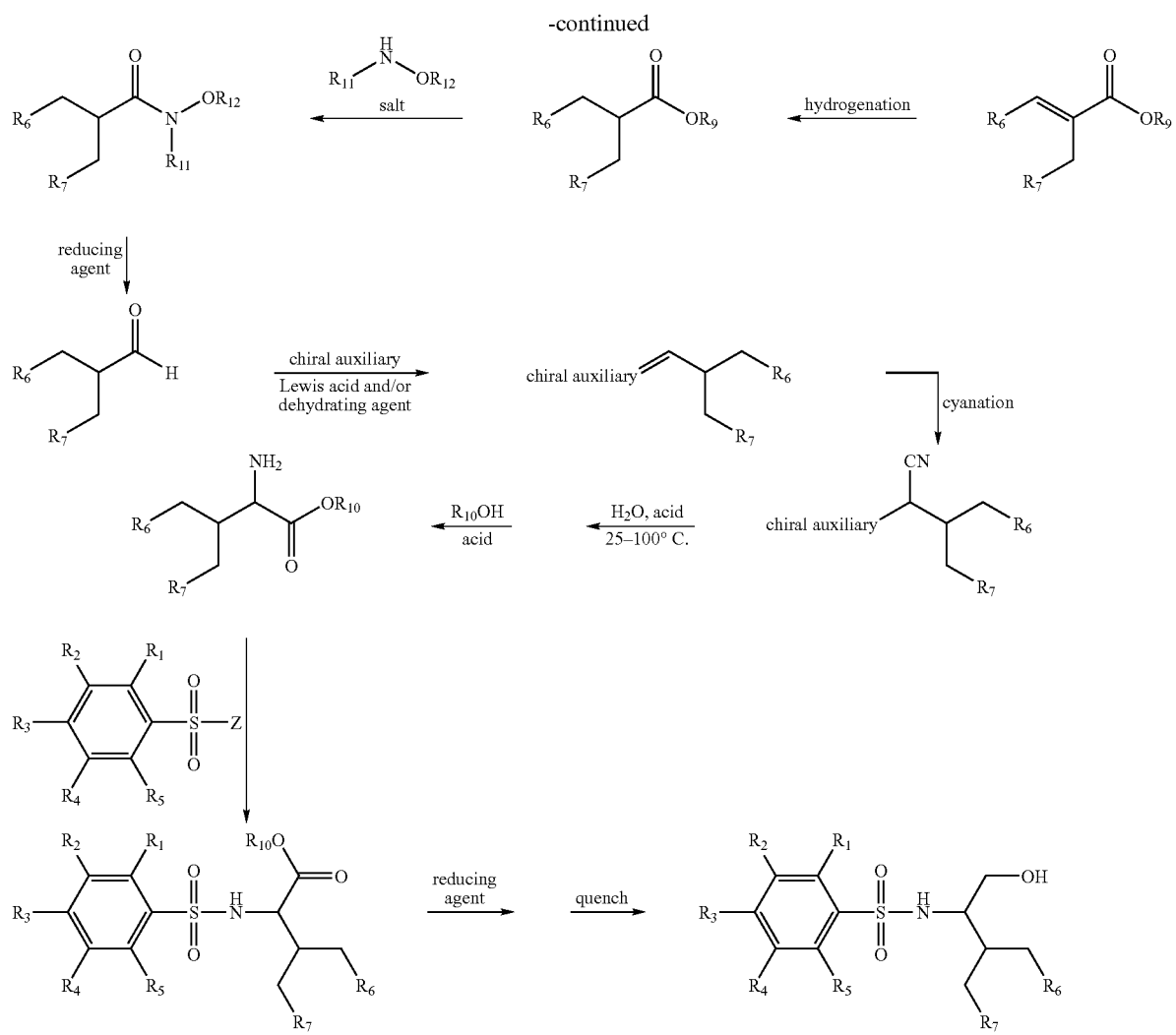

In another embodiment, methods for preparing 4-chloro-N-[(1S)-4,4,4-trifluoro-1-hydroxymethyl-2-(2,2,2-trifluoroethyl)-butyl]benzenesulfonamide, or a pharmaceutically acceptable salt thereof, are provided.

The term "alkyl" is used herein to refer to both straight- and branched-chain saturated aliphatic hydrocarbon groups having one to ten carbon atoms (e.g., $C_1$, $C_2$, $C_3$, $C_4$, $C_5$, $C_6$, $C_7$, $C_8$, $C_9$, or $C_{10}$), such as one to eight carbon atoms (e.g., $C_1$, $C_2$, $C_3$, $C_4$, $C_5$, $C_6$, $C_7$, or $C_8$), one to six carbon atoms (e.g., $C_1$, $C_2$, $C_3$, $C_4$, $C_5$, or $C_6$), or one to four carbon atoms (e.g., $C_1$, $C_2$, $C_3$, or $C_4$). The term "lower alkyl" refers to straight- and branched-chain saturated aliphatic hydrocarbon groups having one to six carbon atoms (e.g., $C_1$, $C_2$, $C_3$, $C_4$, $C_5$, or $C_6$), desirably one to four carbon atoms (e.g., $C_1$, $C_2$, $C_3$, or $C_4$).

The term "alkoxy" is used herein to refer to the O(alkyl) group, where the point of attachment is through the oxygen-atom and the alkyl can be optionally substituted. The term "lower alkoxy" refers to alkoxy groups as just described wherein the alkyl group has one to six carbon atoms (e.g., $C_1$, $C_2$, $C_3$, $C_4$, $C_5$, or $C_6$), desirably one to four carbon atoms (e.g., $C_1$, $C_2$, $C_3$, or $C_4$).

The term "halogen" refers to Cl, Br, F, or I.

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, phenanthryl, and indane. Desirably, aryl refers to a carbocyclic aromatic system having about 6 to about 14 carbon atoms.

The term "substituted aryl" refers to aryl as just defined having one to four substituents including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The pharmaceutically acceptable salts are those derived from such organic and inorganic bases as sodium hydroxide, potassium hydroxide, calcium hydroxide, magnesium hydroxide, diethanolamine, ethylenediamine and similarly known acceptable bases. Prodrugs of the compounds discussed herein may be produced and utilized by one skilled in the art.

In the preparation of the substituted phenylsulfonamide compounds identified above, the first step of the method includes reacting $R_6CH_2CH_2X$, wherein X is halogen, with a phosphine. In one embodiment, $R_6$ is $CF_3(CF_sH_r)_p$, p is 0 to 20; r and s are, independently, 0 to 2, provided that r+s=2, and X is I. In one example, $R_6CH_2CH_2X$ is 1,1,1-trifluoro-3-iodopropane. Suitable phosphines useful in this first step include, without limitation, $P(R_8)_3$, wherein $R_8$ is aryl or alkoxy. In one example, $R_8$ is phenyl, i.e., $P(R_8)_3$ is triphenylphospine. Desirably, the phosphine is used in an excess over the $R_6CH_2CH_2X$ reagent. More desirably, at least a three molar excess of the phosphine is used. By doing so, a phosphonium compound, phosphonate compound, or combination thereof of the following structure is formed, wherein $R_6$, $R_8$, and X are defined herein. In one embodiment, the phosphonium compound is (3,3,3-trifluoropropyl)-triphenylphosphonium iodide.

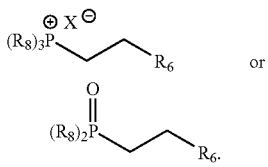

The phosphonium and/or phosphonate compound is then reacted with a first base at a temperature of about −70° C. to about 25° C. A number of bases can be utilized and include, without limitation, lithium bis(trimethylsilyl)amide (LiNH(TMS)$_2$), potassium bis(trimethylsilyl)amide, and lithium diisopropylamide. Desirably, the reaction is performed at a temperature of about −10° C. to about 0° C. In one example, the reaction is performed at a temperature of about −5° C.

This reaction mixture is then reacted with an ester of the formula $YC(O)OR_9$, wherein Y is halogen and $R_9$ is alkyl. In one embodiment, $R_9$ is $CH_2CH_3$ and Y is Cl, i.e., $YC(O)OR_9$ is ethylchloroformate. Desirably, this reaction is performed at a temperature below about −20° C. In one example, the temperature is about −60° C. to about −80° C. In another example, the temperature is about −75° C. By doing so, an organophosphorus compound of the following structure is prepared, wherein $R_6$, $R_8$, and $R_9$ are defined herein:

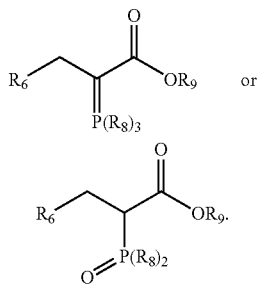

In one embodiment, the following organophosphorus compound, i.e., ylide, is prepared, wherein $R_6$, $R_8$, and $R_9$ are defined above:

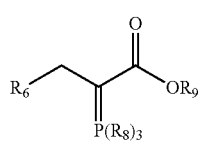

In another embodiment, the following organophosphorus compound may be prepared, wherein $R_6$, $R_8$, and $R_9$ are defined above:

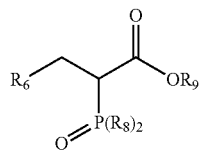

In one embodiment, 4,4,4-trifluoro-2-(triphenyl-$\lambda^5$-phosphanylidene)-butyric acid ester is prepared.

The organophosphorus compound is thereby isolated using techniques known to those of skill in the art which include trituration, recrystallization, and chromatography, among other techniques. Desirably, the organophosphorus compound is isolated by trituration, and more desirably, hydrocarbon trituration. A number of hydrocarbons can be utilized for the trituration and include, without limitation, hexane, pentane, and heptane. Desirably, the hydrocarbon is hexane.

The isolated organophosphorus compound is then reacted with an aldehyde such as $R_7CHO$. Desirably, the aldehyde is dehydrated and free of acidic impurities. The term "acid impurity" as used herein refers to an acidic chemical compound, such as an acid, that can be neutralized. In one embodiment, the acidic impurity is an acid. In another embodiment, the acidic impurity is an organic or inorganic acid. In a further embodiment, the acidic impurity is an inorganic acids including, without limitation, hydrochloric acid, hydrobromic acid, hydroiodic acid, sulfuric acid, nitric acid, and phosphoric acid, among others. In yet another embodiment, the acidic impurity is an organic acids including, without limitation, lactic acid, formic acid, acetic acid, fumaric acid, citric acid, propionic acid, oxalic acid, succinic acid, glycolic acid, glucuronic acid, maleic acid, furoic acid, glutamic acid, benzoic acid, anthranilic acid, salicylic acid, tartaric acid, malonic acid, mallic acid, phenylacetic acid, mandelic acid, embonic acid, methanesulfonic acid, ethanesulfonic acid, panthenoic acid, benzenesulfonic acid, toluenesulfonic acid, stearic acid, sulfanilic acid, alginic acid, and galacturonic acid, among others. Suitably, the acidic impurities are removed using a neutralizing agent. Suitable neutralizing agents are known and available in the art and include sodium bicarbonate and potassium carbonate, among others. The aldehyde is also dehydrated using a dehydrating agent and a water-immiscible solvent. A number of suitable dehydrating agents may be selected by one of skill in the art and include magnesium oxide or magnesium sulfate (MgSO$_4$), among others. Similarly, water-immiscible solvents useful for the dehydration may be selected and include, without limitation, methyl tert-butyl ether (MTBE) and diethyl ether. In one example, the aldehyde is $CF_3(CH_mF_q)_nCHO$. In another example, the aldehyde is trifluoroacetaldehyde. By doing so, an unsaturated ester of the following structure is prepared, wherein $R_6$, $R_7$, and $R_9$ are defined herein:

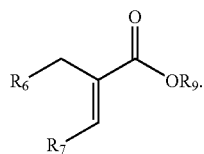

In one example, $R_6$ is $CF_3(CH_mF_q)_n$, $R_7$ is $CF_3(CF_sH_r)_p$, $R_9$ is alkyl; n and p are, independently, 0 to 20; m, q, r, and s are, independently, 0 to 2, provided that m+q=2 and r+s=2. Desirably, $R_9$ is $CH_2CH_3$ and/or n and p are 0. In one embodiment, the unsaturated ester prepared according to this step is of the following structure, wherein $R_9$, m, n, p, q, r, and s are defined herein:

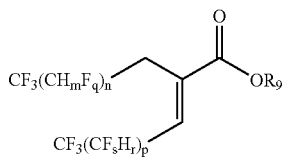

This unsaturated ester is prepared by reacting an aldehyde of the formula $CF_3(CH_mF_q)_nCHO$ with a phosphonium compound of the following structure, wherein $R_8$, $R_9$, p, r, and s are defined herein:

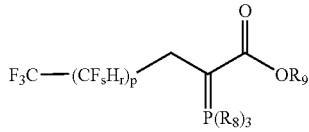

In another embodiment, the unsaturated ester prepared according to this step is 4,4,4-trifluoro-2-(2,2,2-trifluoroethyl)-but-2-enoic acid ester.

The unsaturated ester from the previous step is then hydrogenated to form a compound of the structure:

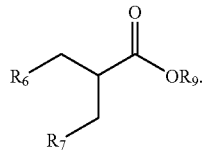

A number of hydrogenating agents are useful in this step and include those hydrogenating agents set forth in Augustine, R. L., Catalytic Hydrogenation, Techniques and Applications in Organic Synthesis, New York, M. Dekker, 1965 and Rylander, P. N., Catalytic Hydrogenation in Organic Syntheses, New York: Academic Press, 1979, which are hereby incorporated by reference. Desirably, the hydrogenating agent includes hydrogen in the presence of a catalyst. Suitable hydrogenating agents include Pd/C, Pd/Al$_2$O$_3$, Pt/C, and Raney Ni, among others. The hydrogenation is optionally performed at elevated temperatures and pressures. In one example, the hydrogenation is performed at 50 psi and 45° C. In one embodiment, 4,4,4-trifluoro-2-(2,2,2-trifluoroethyl)-butyric acid ester is prepared via the hydrogenation step.

The hydrogenated ester is then reacted with an alkylated hydroxylamine salt in the presence of a second base, such as a Grignard reagent including, without limitation, iso-propylmagnesium chloride, to form an amide of the following structure, wherein $R_6$, $R_7$, $R_{11}$, and $R_{12}$ are defined herein. Desirably, the alkylated hydroxylamine salt is a N,O-dialkylhydroxylamine salt. More desirably, the alkylated hydroxylamine is $R_{11}$—NH—$OR_{12}$, wherein $R_{11}$ and $R_{12}$ are, independently, alkyl. In one example, $R_{11}$ and $R_{12}$ are $CH_3$, n is 0, and p is 0. In another example, the alkylated hydroxylamine salt is N,O-dimethylhydroxylamine hydrochloride.

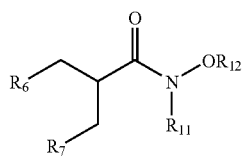

In another embodiment, the following compound is prepared according to this step, wherein $R_{11}$, $R_{12}$, m, n, p, q, r, and s are defined herein:

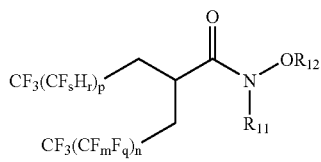

In a further embodiment, the following compound is prepared according to this step, wherein $R_6$ and $R_7$ are defined herein:

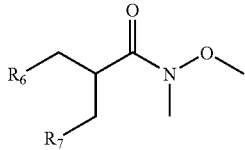

In another embodiment, 4,4,4-trifluoro-N-methoxy-N-methyl-2-(2,2,2-trifluoroethyl)-butyramide is prepared according to this step.

The amide is then reacted with a first reducing agent to form an aldehyde. A number of reducing agents useful in this reduction are known to those of skill in the art and include diisobutylaluminum hydride (DIBAL-H) and lithium aluminum hydride (LiAlH$_4$), among others. Desirably, the reducing agent is DIBAL-H. The reduction is typically performed at reduced temperatures. In one example, the reduction is performed at a temperature of about −70° C. A compound of the following structure is thereby prepared according to this step, wherein $R_6$ and $R_7$ are defined herein:

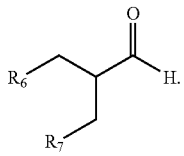

In one embodiment, the aldehyde prepared in this step is of the following structure:

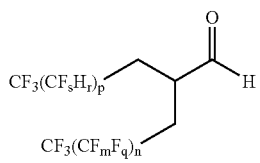

wherein, n and p are, independently, 0 to 20; m, q, r, and s are, independently, 0 to 2, provided that m+q=2 and r+s=2. In one example, n and p are 0. In another embodiment, the aldehyde prepared in this step is 4,4,4-trifluoro-2-(2,2,2-trifluoroethyl)-butyraldehyde.

The aldehyde is then reacted with a chiral auxiliary compound and one or more of a Lewis acid and/or dehydrating agent. Suitable dehydrating agents for use in this step include titanium alkoxides such as titanium ethoxide and titanium propoxide including titanium isopropoxide (Ti($^i$OPr)$_4$), magnesium sulfate, and 4 Å molecular sieves, among others, to form a compound of the structure, wherein $R_6$ and $R_7$ are defined herein. In one embodiment, N-methyl-N-[(1S)-4,4,4-trifluoro-2-(2,2,2-trifluoroethyl)-butylidene]benzenesulfinamide is prepared.

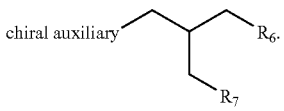

The term "chiral auxiliary compound" as used herein refers to a chemical compound that contains a chiral auxiliary group. As is known in the art, the chiral auxiliary group introduces chirality to the compound it is bound to. A number of chiral auxiliary compounds can be utilized and include sulfinimides, among others. In one example, the chiral auxiliary compound is (S)-p-toluenesulfinamide. Several Lewis acids can be utilized and readily selected by one of skill in the art and include, without limitation, titanium alkoxides. In one example, the Lewis acid is titanium isopropoxide.

The compound previously prepared is then cyanated to form a compound of the following structure, wherein $R_6$ and $R_7$ are defined above. In one embodiment, the cyanated compound is N-methyl-benzenesulfinic acid [(1S)-1-cyano-4,4,4-trifluoro-2-(2,2,2-trifluoroethyl)-butyl]amide. A number of reagents could be utilized for the cyanation and include, without limitation, diethylaluminum cyanide (AlEt$_2$CN) or ethylisopropoxy cyanide.

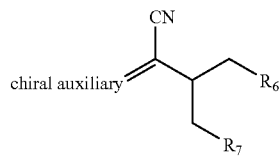

The cyanated compound is then reacted with an aqueous acid. The term "aqueous acid" as used herein includes an acid admixed with water. Aqueous acids that are suitable for use in this step include, without limitation, hydrochloric acid. Desirably, this reaction is performed at a temperature of about 25 to about 100° C. More desirably, the temperature is about 100° C.

This cyanated compound is then reacted with an alcohol in the presence of an acid, which can be an inorganic or organic acid. In one embodiment, the alcohol is $R_{10}$OH, where $R_{10}$ is alkyl, substituted alkyl, aryl, substituted aryl, benzyl or substituted benzyl. In one example, the alcohol is methanol. The acid utilized in this step can be an inorganic or organic acid and is readily selected by one of skill in the art. A number of inorganic acids are known and include hydrochloric acid, hydrobromic acid, hydroiodic acid, sulfuric acid, nitric acid, and phosphoric acid, among others. Similarly, a variety of organic acids are known and include, without limitation, lactic acid, formic acid, acetic acid, fumaric acid, citric acid, propionic acid, oxalic acid, succinic acid, glycolic acid, glucuronic acid, maleic acid, furoic acid, glutamic acid, benzoic acid, anthranilic acid, salicylic acid, tartaric acid, malonic acid, mallic acid, phenylacetic acid, mandelic acid, embonic acid, methanesulfonic acid, ethanesulfonic acid, panthenoic acid, benzenesulfonic acid, toluenesulfonic acid, stearic acid, sulfanilic acid, alginic acid, and galacturonic acid, among others. In one example, the acid is hydrochloric acid or sulfuric acid. In another example, the acid is hydrochloric acid. By doing so, an ester of the following structure is prepared, wherein $R_6$, $R_7$, and $R_{10}$ are defined herein:

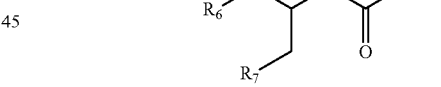

In one embodiment, (2S)-2-amino-5,5,5-trifluoro-3-(2,2,2-trifluoroethyl)-pentanoic acid methyl ester is prepared.

The previously prepared ester is then reacted with a sulfonyl compound of the following structure, wherein Z is halogen and $R_1$-$R_5$ are defined herein. In one embodiment, the sulfonyl compound is 4-chlorobenzenesulfonyl chloride.

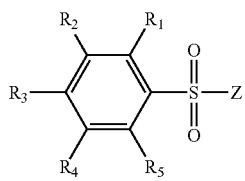

In one embodiment, a compound of the following structure, wherein $R_1$-$R_7$ and $R_{10}$ are defined herein is prepared according to this step. In another embodiment, (2S)-2-(4-chloro-benzenesulfonylamino)-5,5,5-trifluoro-3-(2,2,2-trifluoroethyl)-pentanoic acid methyl ester is prepared.

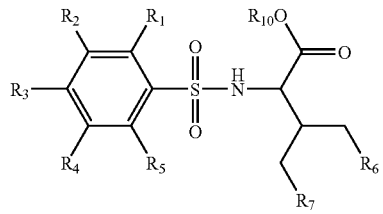

The sulfonylated compound is then reacted with a second reducing agent to form a compound of the structure, wherein $R_1$-$R_7$ are defined herein.

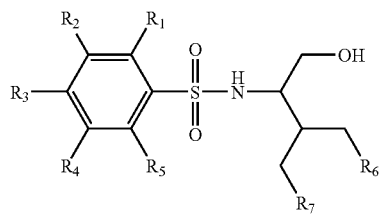

One of skill in the art would readily be able to select a suitable reducing agent for use in this step. Examples of reducing agents useful in this step include those set forth in Seyden-Penne, J., Reductions by the Alumino- and Borohydrides in Organic Synthesis, VCH Publishers, 1991. Desirably, the reducing agent is lithium borohydride ($LiBH_4$) or $LiAlH_4$, among others.

The reduction step is then quenched using an alcohol or water. One of skill in the art would readily be able to select a suitable alcohol for use in the quenching step. Desirably, the alcohol includes, without limitation, methanol, ethanol, or isopropanol. The sulfonamide compound is then isolated using techniques known to those of skill in the art including, without limitation, extraction, filtration, chromatography, recrystallization, and precipitation.

In one embodiment, a method for preparing a compound of the structure is provided:

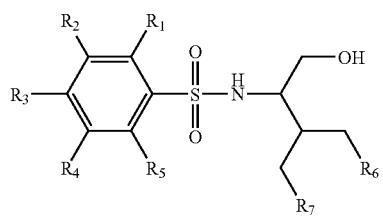

wherein, $R_1$ through $R_5$ are, independently, selected from among hydrogen, halogen, lower alkyl, lower alkoxy, $OCF_3$, $OCF_2H$, $CF_3$, $NO_2$, $CN$, $CH_3CO$, and $SCH_3$; $R_6$ and $R_7$ are, independently, selected from among lower alkyl, $CF_3(CF_sH_r)_p$ and $CF_3(CH_mF_q)_n$, wherein, n and p are, independently, 0 to 20; m, q, r, and s are, independently, 0 to 2, provided that m+q=2 and r+s=2; the method including (a) reacting $R_6CH_2CH_2X$, wherein X is halogen, with $P(R_8)_3$, wherein $R_8$ is aryl or alkoxy, to form a compound of the structure:

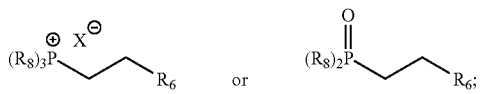

(b) reacting the product of step (a) and a first base at a temperature of about −70° C. to about 25° C.; (c) reacting the product of step (b) with $YC(O)OR_9$, wherein Y is halogen and $R_9$ is alkyl, at a temperature below about −20° C. to form a compound of the structure:

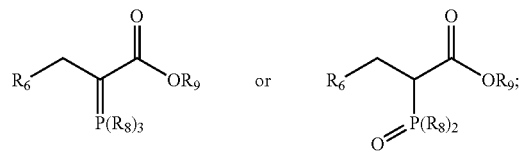

(d) isolating the product of step (c) by hydrocarbon trituration; (e) reacting dehydrated $R_7CHO$, which is also free from acidic impurities, and the product of step (d) to form a compound of the structure:

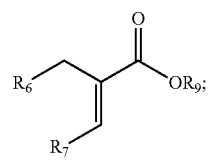

(f) hydrogenating the product of step (e) to form a compound of the structure:

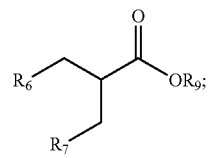

(g) reacting the product of step (f) with a N,O-dialkylhydroxylamine hydrochloride and a second base to form a compound of the structure:

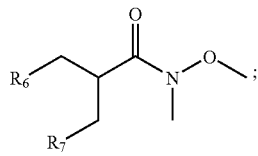

(h) reacting the product of step (g) with a first reducing agent to form a compound of the structure:

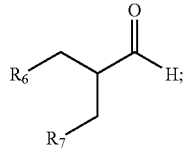

(i) reacting the product of step (h), a chiral auxiliary compound, and one or more of a Lewis acid and dehydrating agent, to form a compound of the structure:

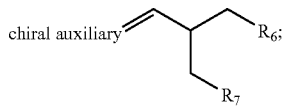

(j) cyanating the product of step (i) to form a compound of the structure:

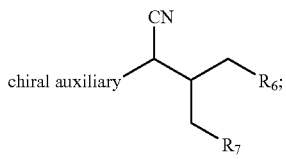

(k) reacting the product of step (j) and an aqueous acid; (l) reacting the product of step (k) with $R_{10}OH$, where $R_{10}$ is alkyl, substituted alkyl, aryl, substituted aryl, benzyl, or substituted benzyl in the presence of an acid, to form a compound of the structure:

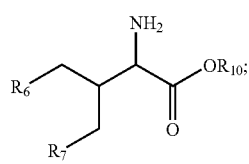

(m) reacting the product of step (l) with a sulfonyl compound of the structure:

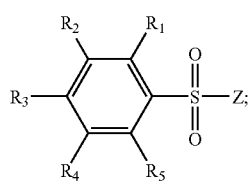

wherein, Z is halogen, to form a compound of the structure:

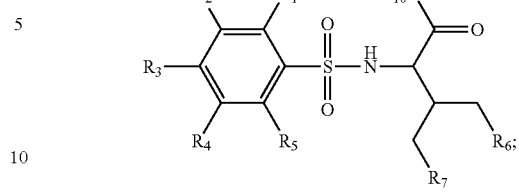

(n) reacting the product of step (m) with a second reducing agent; and (o) quenching the reaction of step (n) to form the compound of the structure:

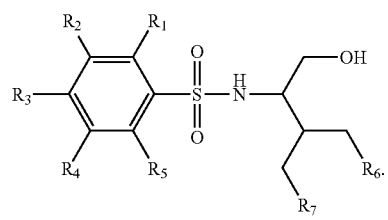

In another embodiment, a method for preparing 4-chloro-N-[(1S)-4,4,4-trifluoro-1-hydroxymethyl-2-(2,2,2-trifluoroethyl)-butyl]benzenesulfonamide is provided and includes (a) reacting 1,1,1-trifluoro-3-iodopropane with triphenylphosphine to form (3,3,3-trifluoropropyl)-triphenylphosphonium iodide; (b) reacting (3,3,3-trifluoropropyl)-triphenylphosphonium iodide and a base at a temperature of −70° C. to 25° C.; (c) reacting the product of step (b) with ethylchloroformate at a temperature below about −20° C. to form 4,4,4-trifluoro-2-(triphenyl-$\lambda^5$-phosphanylidene)-butyric acid ester; (d) isolating 4,4,4-trifluoro-2-(triphenyl-$\lambda^5$-phosphanylidene)-butyric acid ester by hydrocarbon trituration; (e) reacting dehydrated trifluoroacetaldehyde, which is free of acidic impurities, and 4,4,4-trifluoro-2-(triphenyl-$\lambda^5$-phosphanylidene)-butyric acid ester to form 4,4,4-trifluoro-2-(2,2,2-trifluoroethyl)-but-2-enoic acid ester; (f) hydrogenating 4,4,4-trifluoro-2-(2,2,2-trifluoroethyl)-but-2-enoic acid ester to form 4,4,4-trifluoro-2-(2,2,2-trifluoroethyl)-butyric acid ester; (g) reacting 4,4,4-trifluoro-2-(2,2,2-trifluoroethyl)-butyric acid ester with N,O-dimethylhydroxylamine hydrochloride to form 4,4,4-trifluoro-N-methoxy-N-methyl-2-(2,2,2-trifluoroethyl)-butyramide; (h) reacting 4,4,4-trifluoro-N-methoxy-N-methyl-2-(2,2,2-trifluoroethyl)-butyramide with a first reducing agent to form 4,4,4-trifluoro-2-(2,2,2-trifluoroethyl)-butyraldehyde; (i) reacting 4,4,4-trifluoro-2-(2,2,2-trifluoroethyl)-butyraldehyde, a titanium alkoxide, and (S)-(+)-p-toluenesulfinamide to form N-methyl-N-[(1S)-4,4,4-trifluoro-2-(2,2,2-trifluoroethyl)-butylidene]benzenesulfinamide; (j) cyanating N-methyl-N-[(1S)-4,4,4-trifluoro-2-(2,2,2-trifluoroethyl)-butylidene]benzenesulfinamide to form N-methyl-benzenesulfinic acid [(1S)-1-cyano-4,4,4-trifluoro-2-(2,2,2-trifluoroethyl)-butyl]amide; (k) reacting N-methyl-benzenesulfinic acid [(1S)-1-cyano-4,4,4-trifluoro-2-(2,2,2-trifluoroethyl)-butyl]amide with an aqueous acid; (l) reacting the product of step (k) with an alcohol in the presence of an acid to form (2S)-2-amino-5,5,5-trifluoro-3-(2,2,2-trifluoroethyl)-pentanoic acid methyl ester; (m) reacting (2S)-2-amino-5,5,5-trifluoro-3-(2, 2,2-trifluoroethyl)-pentanoic acid methyl ester with 4-chlorobenzenesulfonyl chloride to form (2S)-2-(4-chloro-benzenesulfonylamino)-5,5,5-trifluoro-3-(2,2,2-trifluoroethyl)-pentanoic acid methyl ester; (n) combining (2S)-2-(4-chloro-benzenesulfonylamino)-5,5,5-trifluoro-3-(2,2,2-trifluoroethyl)-pentanoic acid methyl ester and a second reducing agent to form 4-chloro-N-[(1S)-4,4,4-trifluoro-1-hydroxymethyl-2-(2,2,2-trifluoroethyl)-butyl]benzenesulfonamide; (o) quenching the product of step (n); and (p) isolating the 4-chloro N-[(1S)-4,4,4-trifluoro-1-hydroxymethyl-2-(2,2,2-trifluoroethyl)-butyl]benzenesulfonamide.

In a further embodiment, a method for preparing 4-chloro-N-[(1S)-4,4,4-trifluoro-1-hydroxymethyl-2-(2,2,2-trifluoroethyl)-butyl]benzenesulfonamide is provided as set forth in Scheme 2.

In a further embodiment, a method of preparing a compound of the structure is provided:

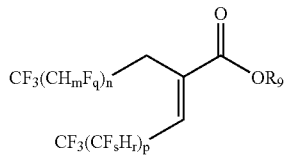

wherein, $R_9$ is alkyl; n and p are, independently, 0 to 20; m, q, r, and s are, independently, 0 to 2, provided that m+q=2 and r+s=2; the method including reacting $CF_3(CH_mF_q)_nCHO$ and an organophosphorus compound of the structure:

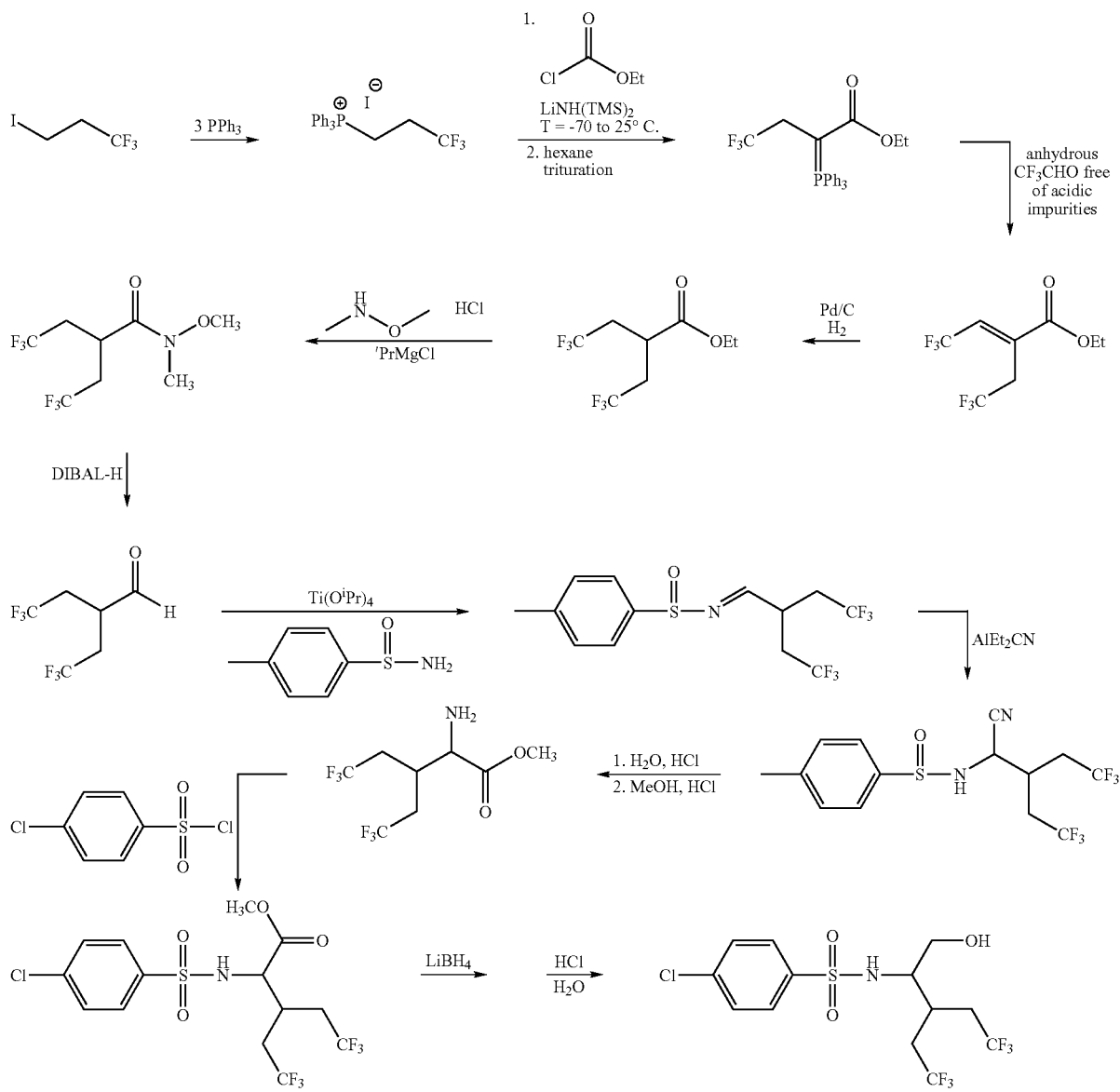

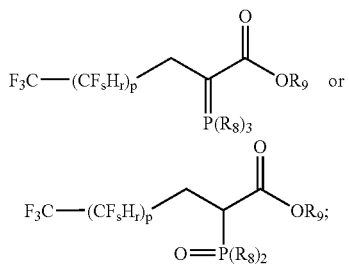

wherein, $R_8$ is aryl or alkoxy.

In yet another embodiment, a method of preparing a compound of the structure is provided:

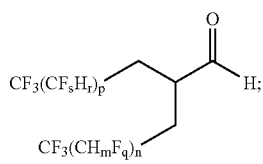

wherein, n and p are, independently, 0 to 20; m, q, r, and s are, independently, 0 to 2, provided that m+q=2 and r+s=2; the method including reacting a reducing agent and a compound of the structure:

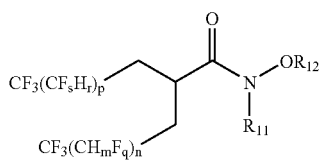

wherein, $R_{11}$ and $R_{12}$ are, independently, alkyl.

The following examples are provided to illustrate the production of representative compounds of the invention. One skilled in the art will appreciate that although specific reagents and conditions are outlined in the following examples, these reagents and conditions are not a limitation on the present invention.

EXAMPLES

Example 1

4-Chloro-N-[(1S)-4,4,4-trifluoro-1-hydroxymethyl-2-(2,2,2-trifluoro-ethyl)-butyl]-benzenesulfonamide

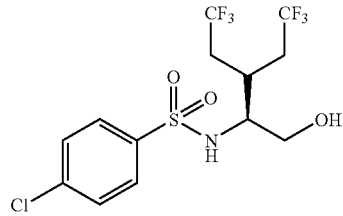

A. (3,3,3-Trifluoropropyl)-triphenylphosphonium iodide

A solution of 1,1,1-trifluoro-3-iodopropane (263.1 g, 1.17 moles) and triphenylphosphine (924.4 g, 3.52 moles) in toluene (950 mL) was stirred at reflux for 12 hours. The solid product precipitated from the reaction mixture throughout the course of the reaction. The reaction was allowed to cool to ambient temperature and then cooled to about 5° C. in an ice bath. The solid precipitate was isolated by filtration and dried in vacuo at 25° C. to give a white powder (526.5 g, 92%).

Anal. Calc'd for $C_{21}H_{19}F_3IP$: C, 51.87; H, 3.94. Found: C, 51.99; H, 3.90.

B. 4,4,4-Trifluoro-2-(triphenyl-$\lambda^5$-phosphanylidene)-butyric acid ethyl ester A suspension of (3,3,3-trifluoropropyl)triphenylphosphonium iodide (194.5 g, 0.4 moles) in tetrahydrofuran (THF—anhydrous, 800 mL) was cooled to −5° C. in an ice/brine bath under nitrogen. Lithium bis(trimethylsilyl)amide (1.0 M in THF, 800 mL, 0.8 moles) was added to this suspension dropwise over 2 hours. The temperature was maintained below 5° C. throughout the addition. The reaction mixture was then cooled to −75° C. in a dry ice/acetone bath. To this solution, ethylchloroformate (76.5 mL, 0.8 moles) was added dropwise over 30 minutes. The reaction was stirred at −75° C. for an additional hour and allowed to warm to 25° C. overnight. The reaction mixture was poured onto brine (1.5 L) and stirred for 30 minutes. The layers were separated and the organic layer was washed with brine (200 mL). The aqueous layer was washed with dichloromethane ($CH_2Cl_2$−2×200 mL) and the combined organics were concentrated to a residue. This residue was redissolved in $CH_2Cl_2$ (500 mL), dried over $MgSO_4$, and filtered through a plug of magnasol. The solvent was reduced to a minimum (~100 mL) in vacuo and the product was precipitated with hexanes (250 mL). The solvent was completely removed in vacuo and the solid product was triturated with hexanes (500 mL). The solid was isolated by filtration and dried overnight in vacuo at 25° C. to give a beige powder 152.8 g, 89%).

Anal. Calc'd for $C_{24}H_{22}F_3O_2P$: C, 66.97; H, 5.15. Found: C, 66.37; H, 5.28.

C. 4,4,4-Trifluoro-2-(2,2,2-trifluoroethyl)-but-2-enoic acid ethyl ester

Trifluoroacetaldehyde hydrate (150 g, technical grade, pH 1) was treated with solid, anhydrous sodium bicarbonate (15 g, powder) with stirring to result in a mildly foaming suspension. Anhydrous magnesium sulfate powder (60 g) was added, followed by addition of MTBE (300 mL) to result in a mildly exothermic reaction. The suspension was kept in a water bath at 10° C. for 10 minutes and filtered through a fluted filter funnel and washed with MTBE (2×250mL). The filtrate (pH 7.2) was charged into a 2L "Parr" pressure reactor containing the starting ylide (204 g, 0.474 mol). Anhydrous magnesium sulfate powder (60 g) was added to this mixture. The reaction vessel was heated to 70-75° C. with stirring for 15 hours. The pressure in the "Parr" reactor rose to 18-21 psi. The reaction was cooled to ambient temperature and the mixture was filtered. The filter cake was washed with MTBE. The filtrate was distilled at 60-70 mm/Hg to remove most of the MTBE in the first fraction and collected the remainder in the second fraction. The pressure for the second fraction was reduced to 20 mm/Hg to yield 121.7 g. The second fraction (121.7 g) was redistilled at 20 mm/Hg with a bath temperature at 80° C. to yield a main fraction of a low viscosity liquid, (103.5 g, 87%) b.p. 53-55° C. Mass Spectrum (+ESI): 251 [M+H]$^+$

D. 4,4,4-Trifluoro-2-(2,2,2-trifluoroethyl)-butyric acid ethyl ester 4,4,4-Trifluoro-2-(2,2,2-trifluoroethyl)-but-2-enoic acid ethyl ester (225 g, 0.9 mol) was dissolved in THF (700 mL) and treated with 5% Pd/C (17 g). The mixture was reduced by hydrogenation in a "Parr" shaker in a 2.5 L pressure bottle at 50 psi. The reaction was exothermic to 45° C. and was controlled by interrupting the shaking motion of the "Parr" shaker. The reaction was completed in approximately 2 hours. The reaction mixture was filtered through a 2-inch bed of the Solka Floc® reagent/magnesium sulfate to give a clear, colorless solution of the title compound (225 g in 1182 g of tetrahydrofuran, quantitative yield). Mass Spectrum (+ESI): 253 [M+H]$^+$

E. 4,4,4-Trifluoro-N-methoxy-N-methyl-2-(2,2,2-trifluoroethyl)butyramide

N,O-Dimethylhydroxylamine hydrochloride (90 g, 092 mol) was added to a solution of 4,4,4-trifluoro-2-(2,2,2-trifluoroethyl)butyric acid ethyl ester (116.28 g, 0.46 mol) in THF (610.8 g weight of the solution). The mixture was cooled to −15 to −20° C. with a dry ice/acetone bath. A solution of i-propyl magnesium chloride (924 mL, 2M in THF, 1.848 mol) was added to the reaction mixture dropwise over a period of 1 hour, keeping the temperature at −15 to −20° C. After the addition, the reaction was stirred at that temperature for 30 minutes.

The reaction was quenched by adding dropwise HCl (2N, 600 ml, 1.2 mol). The reaction proceeded at a very exothermic rate for the first 50 mL. The temperature did not exceed 3° C. Initially, a thick suspension formed which subsequently became a clear solution with two layers.

The mixture was extracted with MTBE (1.5 L). The aqueous phase was re-extracted with MTBE (0.5 L). The combined organic extracts were washed with brine (2×0.5 L). The organic phase was dried over anhydrous magnesium sulfate powder, filtered and the filtrate was concentrated in vacuo at a temperature of equal to or less than 35° C. to an oil of weight of 121 grams. The oil was distilled at 15 mm/Hg/b.p. 68° C. to give the title compound as oil. Mass Spectrum (+ESI): 268 [M+H]$^+$

F. 4,4,4-Trifluoro-2-(2,2,2-trifluoro-ethyl)-butyraldehyde

To a solution of 4,4,4-trifluoro-N-methoxy-N-methyl-2-(2,2,2-trifluoroethyl)-butyramide (2.67 g, 10 mmol) in CH$_2$Cl$_2$ (10 mL) was added diisobutylaluminum hydride (2.9 mL, 16 mmol) over 10 minutes at −70° C. The reaction mixture was stirred at −70° C. for 40 minutes, then transferred via a cannula to a flask containing 30 mL of 2N HCl at 0° C. Ten mL of concentrated HCl was added, and the mixture was stirred at 25° C. for 30 minutes. The phases were split and the aqueous phase was extracted with 5 mL of CH$_2$Cl$_2$. The combined organic phase was washed with brine and dried over MgSO$_4$. NMR analysis of the solution using an internal standard indicated formation of the title product in 65% yield. The solution was used as such for further transformations.

G. 4-Methyl-N-[(1S)-4,4,4-trifluoro-2-(2,2,2-trifluoroethyl)butylidene]benzenesulfinamide Titanium isopropoxide (13.4 mL, 44 mmol, 97% pure) and (S)-(+)-p-toluenesulfinamide were added to a CH$_2$Cl$_2$ solution of 4,4,4-trifluoro-2-(2,2,2-trifluoroethyl)butyraldehyde (92 mL; contained 8.8 mmol of the aldehyde, prepared as described above). The reaction mixture was stirred at 40° C. for 5 hours, cooled to 25° C., and poured into a mixture of CH$_2$Cl$_2$ (100 mL) and water (50 mL) at 0° C. The mixture was stirred at 25° C. for 1 hour and then filtered through the Celite® reagent. The phases were separated and the aqueous phase was extracted with CH$_2$Cl$_2$. The combined organic fraction was washed with brine, dried over MgSO$_4$, and concentrated. The resultant crude mixture was dissolved in 3:7 ethylacetate-heptane (EtOAc-heptane), passed through a pad of silica gel, and concentrated to afford 2.11 g (69%) of the title product. Mass Spectrum (+ESI): 346 [M+H]$^+$

H. 4-Methyl-benzenensulfinic acid [(1S)-1-cyano-4,4,4,-trifluoro-2-(2,2,2-trifluoroethyl)-butyl]amide THF (6 mL) and diethylaluminum cyanide (3 mL of 1M toluene solution, 3 mmol) were placed in a 50-mL flask. Isopropanol (0.153 mL, 2 mmol) was added at 0° C. The mixture was stirred at 0° C. for 15 minutes, then transferred via a cannula to a flask containing THF (18 mL) and 4-methyl-N-[(1S)-4,4,4-trifluoro-2-(2,2,2-trifluoroethyl)butylidene]benzenesulfinamide (0.69 g, 2 mmol) at −70° C. The reaction mixture was warmed up to 25° C. and stirred for 1 hour. The reaction was quenched by the addition of 50 mL of ammonium chloride (NH$_4$Cl) solution at 0° C. The resultant suspension was filtered through the Celite® reagent. The Celite® reagent pad was washed with EtOAc and the phases were separated. The aqueous phase was extracted with EtOAc. The combined organic fraction was washed with brine, dried, and concentrated to afford 0.72 g of the title product as a 10:1 mixture of diastereomers. Mass Spectrum (+ESI): 373 [M+H]$^+$

I. (2S)-2-Amino-5,5,5-trifluoro-3-(2,2,2-trifluoroethyl)-pentanoic acid methyl ester A solution of 4-methyl-benzenensulfinic acid [(1S)-1-cyano-4,4,4-trifluoro-2-(2,2,2-trifluoroethyl)-butyl]amide (10 g, 29 mmol) in concentrated HCl (200 mL) was heated under reflux for 15 hours. The reaction was cooled to 25° C. A by-product, toluene-4-thiosulfonic acid S-p-tolyl ester, separated from the aqueous solution as a white crystalline solid and was filtered off. The aqueous filtrate was concentrated in vacuo to a sticky white solid. The crude amino acid was taken up in concentrated HCl (200 mL) and extracted with toluene (2×50 mL). The aqueous phase was concentrated in vacuo, co-evaporating with toluene (4×70 mL) to give a solid compound. The amino acid was dissolved in methanol (400 mL), treated with anhydrous HCl (4N, 100 mL) and refluxed for 72 hours. The reaction was evaporated in vacuo to a foam (60% ester conversion by NMR). The reaction mixture was dissolved in methanol (300 mL) and treated with ethereal HCl (2N, 100 mL) and refluxed for 24 hours. The solution was concentrated to a solid (80% ester conversion by NMR). The crude mixture was dissolved in water and extracted with MTBE. The aqueous phase was basified with solid sodium bicarbonate (NaHCO$_3$) and extracted with MTBE (2×100 mL). The organic layer was dried over MgSO$_4$, filtered and concentrated in vacuo to give the title compound as a solid. (4.6 g, 62%). Mass Spectrum (+ESI): 268 [M+H]$^+$

J. (2S)-2-(4-Chloro-benzenesulfonylamino)-5,5,5-trifluoro-3-(2,2,2-trifluoro-ethyl)-pentanoic acid methyl ester A solution of 4-chlorobenzenesulfonyl chloride (2.66 g, 12.2 mmol, 97% pure) in CH$_2$Cl$_2$ (7 mL) was added to a solution of (2S)-2-amino-5,5,5-trifluoro-3-(2,2,2-trifluoroethyl)pentanoic acid methyl ester (2.173 g, 8.14 mmol) and pyridine (1.97 mL, 24.4 mmol) in CH$_2$Cl$_2$ (15 mL). The reaction mixture was stirred at 25° C. for 4 hours, then cooled to 0° C. 1N HCl (15 mL) was added followed by dichloromethane (10 mL) and the phases were separated. The organic phase was washed with 1N HCl (15 mL) and brine, dried over Na$_2$SO$_4$, and concentrated to afford 4.1 g of crude mixture as a yellow solid. The solids were recrystallized from heptane (14 mL) to afford 3.035 g of the title product (84% yield). Mass Spectrum (+ESI): 442 [M+H]$^+$

K. 4-Chloro-N-[(1S)-4,4,4-trifluoro-1-hydroxymethyl-2-(2,2,2-trifluoro-ethyl)-butyl]-benzenesulfonamide To a solution of (2S)-2-(4-chloro-benzenesulfonylamino)-5,5,5-trifluoro-3-(2,2,2-trifluoroethyl)pentanoic acid methyl ester (2.924 g, 6.6 mmol) in THF (30 mL) was added LiBH$_4$ (9.9 mL of 2M THF solution, 19.8 mmol) over 10 minutes at 4-6° C. The reaction mixture was stirred at 25° C. for 4 days. Additional LiBH$_4$ (6.6 mL of 2M THF solution, 13.2 mmol) was added, and the reaction mixture was stirred at 25° C. for an additional 24 hours. The reaction mixture was cooled to 0° C. and quenched by slow addition of 30 mL of 2N HCl (vigorous gas evolution). The mixture was partially concentrated in vacuum and extracted with EtOAc. The organic fraction was washed with brine, dried over Na$_2$SO$_4$, and concentrated to afford 2.66 g of crude product. The crude product was dissolved in a mixture of EtOAc (10 mL) and heptane (3 mL) at 55° C., cooled to 25° C., and the resultant suspension was aged for 48 hours. Heptane (27 mL) was added and the mixture was stirred at 25° C. for additional 48 hours. The precipitate was filtered and washed with heptane to afford 1.962 g of the title compound (72% yield), mp: 186-187° C. Chiral HPLC: 97% ee (the Chiralcel® AD column 0.46×25 cm, 10% EtOH in hexanes). HRMS calc. (for M+H): 414.0360. Found: 414.0359.

Anal. Calc'd for C$_{13}$H$_{14}$ClF$_6$NO$_3$S: C, 37.54; H, 3.52; N, 3.20. Found: C, 37.74; H, 3.41; N, 3.39.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A method for preparing a compound of the structure:

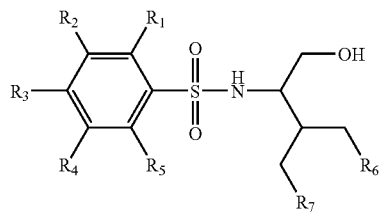

wherein:

R$_1$ through R$_5$ are, independently, selected from the group consisting of hydrogen, halogen, lower alkyl, lower alkoxy, OCF$_3$, OCF$_2$H, CF$_3$, NO$_2$, CN, CH$_3$CO, and SCH$_3$;

R$_6$ and R$_7$ are, independently, selected from the group consisting of lower alkyl, CF$_3$(CF$_s$H$_r$)$_p$ and CF$_3$(CH$_m$F$_q$)$_n$;

n and p are, independently, 0 to 20;

m, q, r, and s are, independently, 0 to 2;

provided that m+q=2 and r+s=2;

said method comprising:

(a) reacting R$_6$CH$_2$CH$_2$X, wherein X is halogen, with P(R$_8$)$_3$, wherein R$_8$ is aryl or alkoxy, to form a compound of the structure:

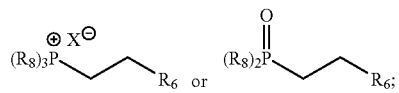

(b) reacting the product of step (a) and a first base at a temperature of about −70° C. to about 25° C.;

(c) reacting the product of step (b) with YC(O)OR$_9$, wherein Y is halogen and R$_9$ is alkyl, at a temperature below about −20° C. to form a compound of the structure:

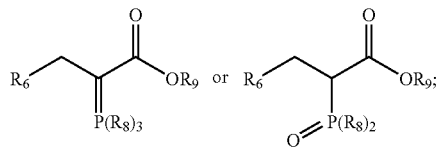

(d) isolating the product of step (c);

(e) reacting dehydrated R$_7$CHO, which is free of acidic impurities, and the product of step (d) to form a compound of the structure:

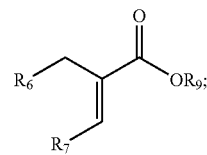

(f) hydrogenating the product of step (e) to form a compound of the structure:

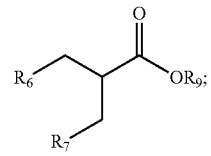

(g) reacting the product of step (f) with a N,O-dialkyl-hydroxylamine hydrochloride and a second base to form a compound of the structure:

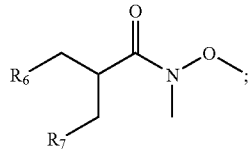

(h) reacting the product of step (g) with a first reducing agent to form a compound of the structure:

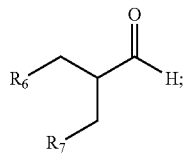

(i) reacting the product of step (h), a chiral auxiliary compound, and one or more of a Lewis acid and dehydrating agent, to form a compound of the structure:

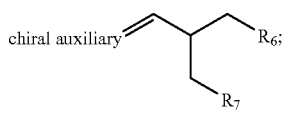

(j) cyanating the product of step (i) to form a compound of the structure:

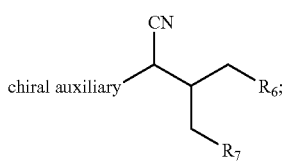

(k) reacting the product of step (j) and an aqueous acid;
(l) reacting the product of step (k) with $R_{10}OH$, where $R_{10}$ is alkyl, substituted alkyl, aryl, substituted aryl, benzyl, or substituted benzyl, in the presence of an acid to form a compound of the structure:

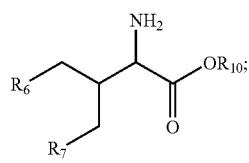

(m) reacting the product of step (l) with a sulfonyl compound of the structure:

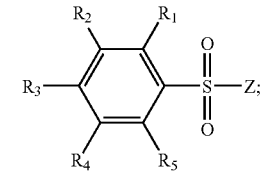

wherein, Z is halogen, to form a compound of the structure:

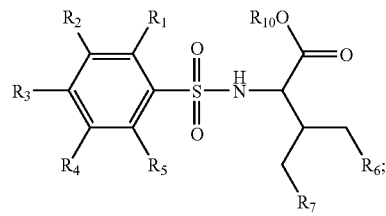

(n) reacting the product of step (m) with a second reducing agent; and
(o) quenching the reaction of step (n).

2. The method according to claim 1, wherein $R_6$ is $CF_3$ $(CF_sH_r)_p$, p is 0, and X is I.

3. The method according to claim 1, wherein $R_6$ is $CF_3$ and X is I.

4. The method according to claim 1, wherein said $R_9$ is $CH_2CH_3$ and Y is Cl.

5. The method according to claim 1, wherein said sulfonyl compound is 4-chlorobenzenesulfonyl chloride.

6. The method according to claim 1, wherein $R_8$ is phenyl.

7. The method according to claim 1, wherein step (a) comprises excess $P(R_8)_3$.

8. The method according to claim 1, wherein $R_7CHO$ is trifluoroacetaldehyde.

9. The method according to claim 1, wherein said N,O-dialkylhydroxylamine hydrochloride is N,O-dimethylhydroxylamine hydrochloride.

10. The method according to claim 1, wherein said Lewis acid is a titanium alkoxide.

11. The method according to claim 10, wherein said titanium alkoxide is titanium isopropoxide.

12. The method according to claim 1, wherein said chiral auxiliary compound is (S)-p-toluenesulfinamide.

13. The method according to claim 1, wherein $R_{10}$ is $CH_3$.

14. The method according to claim 1, wherein step (c) is performed at a temperature of about −60 to about −80° C.

15. The method according to claim 1, wherein said first base is lithium bis(trimethylsilyl)amide.

16. The method according to claim 1, wherein step (b) is performed at a temperature of about −10° C. to about 0° C.

17. The method according to claim 1, wherein said first reducing agent is DIBAL-H.

18. The method according to claim 1, wherein said cyanation is performed using diethylaluminum cyanide or ethylisopropoxy cyanide.

19. The method according to claim 1, wherein step (k) is performed at a temperature of about 25 to about 100° C.

20. The method according to claim 1, wherein said second reducing agent is lithium borohydride.

21. A method for preparing 4-chloro-N-[(1S)-4,4,4-trifluoro-1-hydroxymethyl-2-(2,2,2-trifluoroethyl)-butyl]benzenesulfonamide comprising:

(a) reacting 1,1,1-trifluoro-3-iodopropane with triphenylphosphine to form (3,3,3-trifluoropropyl)-triphenylphosphonium iodide;

(b) reacting said (3,3,3-trifluoropropyl)-triphenylphosphonium iodide and a first base at a temperature of −70° C. to 25° C.;

(c) reacting the product of step (b) with ethylchloroformate at a temperature below about −20° C. to form 4,4,4-trifluoro-2-(triphenyl-$\lambda^5$-phosphanylidene)-butyric acid ester;

(d) isolating said 4,4,4-trifluoro-2-(triphenyl-$\lambda^5$-phosphanylidene)-butyric acid ester by hydrocarbon trituration;

(e) reacting dehydrated trifluoroacetaldehyde, which is free of acidic impurities, and said 4,4,4-trifluoro-2-(triphenyl-$\lambda^5$-phosphanylidene)-butyric acid ester to form 4,4,4-trifluoro-2-(2,2,2-trifluoroethyl)-but-2-enoic acid ester;

(f) hydrogenating said 4,4,4-trifluoro-2-(2,2,2-trifluoroethyl)-but-2-enoic acid ester to form 4,4,4-trifluoro-2-(2,2,2-trifluoroethyl)-butyric acid ester;

(g) reacting said 4,4,4-trifluoro-2-(2,2,2-trifluoroethyl)-butyric acid ester with N,O-dimethylhydroxylamine hydrochloride to form 4,4,4-trifluoro-N-methoxy-N-methyl-2-(2,2,2-trifluoroethyl)-butyramide;

(h) reacting said 4,4,4-trifluoro-N-methoxy-N-methyl-2-(2,2,2-trifluoroethyl)-butyramide with a first reducing agent to form 4,4,4-trifluoro-2-(2,2,2-trifluoroethyl)-butyraldehyde;

(i) reacting said 4,4,4-trifluoro-2-(2,2,2-trifluoroethyl)-butyraldehyde, a titanium alkoxide, and (S)-(+)-p-toluenesulfinamide to form N-methyl-N-[(1S)-4,4,4-trifluoro-2-(2,2,2-trifluoroethyl)-butylidene]benzenesulfinamide;

(j) cyanating said N-methyl-N-[(1S)-4,4,4-trifluoro-2-(2,2,2-trifluoroethyl)-butylidene]benzenesulfinamide to form N-methyl-benzenesulfinic acid [(1S)-1-cyano-4,4,4-trifluoro-2-(2,2,2-trifluoroethyl)-butyl]amide;

(k) reacting said N-methyl-benzenesulfinic acid [(1S)-1-cyano-4,4,4-trifluoro-2-(2,2,2-trifluoroethyl)-butyl]amide with an aqueous acid;

(l) reacting the product of step (k) with an alcohol in the presence of an acid to form (2S)-2-amino-5,5,5-trifluoro-3-(2,2,2-trifluoroethyl)-pentanoic acid methyl ester;

(m) reacting said (2S)-2-amino-5,5,5-trifluoro-3-(2,2,2-trifluoroethyl)-pentanoic acid methyl ester with 4-chlorobenzenesulfonyl chloride to form (2S)-2-(4-chlorobenzenesulfonylamino)-5,5,5-trifluoro-3-(2,2,2-trifluoroethyl)-pentanoic acid methyl ester;

(n) combining said (2S)-2-(4-chloro-benzenesulfonylamino)-5,5,5-trifluoro-3-(2,2,2-trifluoroethyl)-pentanoic acid methyl ester and a second reducing agent;

(o) quenching the product of step (n); and (p) isolating said 4-chloro-N-[(1S)-4,4,4-trifluoro-1-hydroxymethyl-2-(2,2,2-trifluoroethyl)-butyl]benzenesulfonamide.

* * * * *